Figure 1:
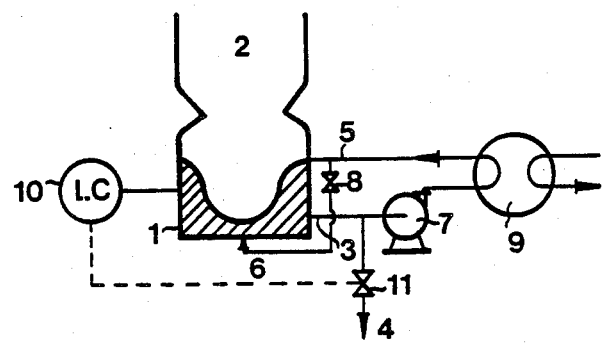

United States Patent [19]

Goorden et al.

[11] Patent Number: 4,654,437

[45] Date of Patent: Mar. 31, 1987

[54] PROCESS OF RECOVERING PURIFIED BENZOIC ACID

[75] Inventors: Josephus J. P. M. Goorden, Sittard; Antonius J. F. Simons, Geleen; Ludovicus A. L. Kleintjens, Stein, all of Netherlands

[73] Assignee: Stamicarbon, B.V., Geleen, Netherlands

[21] Appl. No.: 795,642

[22] Filed: Nov. 6, 1985

[30] Foreign Application Priority Data

Nov. 23, 1984 [NL] Netherlands ........................ 8403558

[51] Int. Cl.$^4$ ............................................. C07C 51/42
[52] U.S. Cl. .................................................. 562/494
[58] Field of Search ........................................ 562/494

[56] References Cited

U.S. PATENT DOCUMENTS 2,189,726  2/1940  Conover .............................. 562/494
3,235,588  2/1966  Weaver ............................... 562/494
4,547,587  10/1985  Kleintjens et al. ................. 562/494

*Primary Examiner*—Paul J. Killos
*Attorney, Agent, or Firm*—Cushman, Darby & Cushman

[57] ABSTRACT

Process for recovering benzoic acid purified by means of a supercritical extraction of solid benzoic acid, characterized in that after the extraction the purified benzoic acid is remelted at least in part and is carried off from the melting device in at least partly liquid form.

6 Claims, 1 Drawing Figure

PROCESS OF RECOVERING PURIFIED BENZOIC ACID

The invention relates to a process for recovering purified benzoic acid, which has beeen purified by means of a supercritical extraction of solid benzoic acid.

In the supercritical extraction of solid benzoic acid for the purpose of removing impurities like diphenyl oxide, as described for instance in the Netherlands patent application No. 8300008 laid open to public inspection, the purified solid must be removed from the extractor after the extraction. The design of the processes known for this removal is usually batchwise. This is due to the fact that the semi-continuous or continuous removal of the solid from the high pressure section in which the supercritical extraction is carried out is a usually insuperable technical obstacle.

In the present state of the art transportation systems are known for this purpose, in which connection reference is made to VDI-Berichten no. 409, 1981 and U.S. Pat. No. 3,190,701. The possibilities for solids removal systems are closely related to the morphology, the running characteristics, the hardness and brittleness of the solid, which may result in wearing of parts like valves and other moving parts.

Moreover, care must be taken that, before its removal to an environment of atmospheric pressure, the extracted solid phase is cleared of the extract phase, which may be laden with the extracted impurities. To this end, for instance, flushing or washing with pure extractant will be necessary in practice. This will result in a loss of extractant, as well as in extra compression costs of extractant to be newly supplied.

Now the object of the invention is to provide a process for a continuous removal of the purified benzoic acid with a drastic reduction of the loss extractant.

The invention therefore relates to a process for recovering benzoic acid purified by means of a supercritical extraction of solid benzoic acid, which process is characterized in that the purified benzoic acid thus obtained is remelted at least in part and is carried off from the melting device in at least partly liquid form.

By applying the process according to the invention purified benzoic acid obtained by supercritical extraction can be recovered while the objections inherent in the transportation of a solid are avoided by carrying off the benzoic acid in at least partly liquid form.

As the solubility of the extractant in liquid benzoic acid is lower than the volume fraction of empty space between the crystals occupied by the extractant in the removal of the benzoic acid, a substantial reduction of the loss of extractant is obtained, while at the same time the benzoic acid need no longer be cleared, before its removal, of the impurities-laden extract phase, for instance by flushing or washing with pure extractant.

In the melting device preference is given to applying a pressure approximately equalling the pressure applied in the extraction of the benzoic acid. A pressure drop in the transfer from the extraction space to the melting device is then avoided, because part of the extracted impurities can then be deposited again on the purified benzoic acid. As in the extraction a pressure of at least 3 MPa is applied, a pressure of at least 3 MPa is preferably applied also in the melting device.

The remelting of the benzoic acid crystals can preferably be effected by keeping part of the liquid material carried off in circulation over the melting device. The heat required for the melting of the crystals is supplied to the circulated flow via heat exchange with this flow.

In order to come to a proper transfer of heat between the circulated flow and the crystals and in order to take care that a substantially liquid phase is drained off, preference is given to the recirculated flow, as well as the flow of liquid material carried off, being tangentially supplied to, respectively removed from, the bottom section of the melting device. This results in the presence of a vortex in the melting device. It is not necessary to carry off a complete melt from the melting device. This depends on the manner in which later in the process the liquid phase is processed. The chosen solids concentration in the circulated flow is then preferably such that it is nowhere in excess of 20% (wt), because otherwise clogging may occur.

It may be clear that preferably care is taken to supply the solid benzoic acid to the melting device gradually. This gradual supply must be in agreement with the melting capacity of the melting device and the desired degree of melting.

The invention is further elucidated by means of the attached drawing without limiting the invention hereto.

FIG. 1 represents a vertical section of the device.

Melting device 1 is provided with a feed 2, a tangential outlet 3, a tangential feed 5, a central feed 6 and a drain 4.

Melting device 1 of the device in operation for recovering benzoic acid contains a suspension of the benzoic acid in its own melt. This suspension is pumped continuously through a pump 7 via a heater 9 from outlet 3 to feeds 5 and 6. From the extraction the solid benzoic acid is supplied via feed 2 to the circulating suspension. The return of the suspension to melting device 1 is partly effected via the central feed 6. Because a vortex is formed by the circulation in melting device 1, the partial feedback of the suspension via feed 6 is important to guarantee a proper flooding of the bottom of mixing vessel 1. The apportionment of the suspension fed back to the mixing vessel between feeds 5 and 6 can be set by means of a control valve 8.

Via drain 4 part of the circulating suspension, equalling the amount of benzoic acid fed to the melting device, is withdrawn from the system, which can be controlled preferably via a level control 10, which controls the material carried off via control valve 11.

We claim:

1. A process for recovering benzoic acid purified by means of a supercritical extraction of impurities from solid benzoic acid comprising the steps of:
   removing said purified benzoic acid from the extractor to a melting device;
   heating said benzoic acid in said melting device to form a suspension of the solid benzoic acid in its own melt;
   removing said suspension of benzoic acid from said melting device.

2. A process as claimed in claim 1 wherein said purified benzoic acid is removed from the extractor to the melting device at constant pressure.

3. Process according to claim 1, characterized in that at least part of the liquid drain is recirculated to the melting device via a heat exchanger.

4. Process according to claim 3, characterized in that the recirculated flow is fed tangentially into the melting device.

5. Process according to claim 1, characterized in that a pressure of at least 3 MPa is applied.

6. Process according to claim 3, characterized in that the concentration of solids in the circulated flow is lower than 20% (wt).

* * * * *